(12) United States Patent
Kashyap

(10) Patent No.: US 6,932,764 B2
(45) Date of Patent: Aug. 23, 2005

(54) MULTIPURPOSE CIRCULAR RETRACTOR

(76) Inventor: Ravindra Kashyap, 225 79th St., Brooklyn, NY (US) 11209

( * ) Notice: Subject to any disclaimer, the term of this patent is extended or adjusted under 35 U.S.C. 154(b) by 106 days.

(21) Appl. No.: 10/300,354

(22) Filed: Nov. 20, 2002

(65) Prior Publication Data

US 2003/0097045 A1 May 22, 2003

Related U.S. Application Data

(60) Provisional application No. 60/331,837, filed on Nov. 20, 2001.

(51) Int. Cl.[7] ............................................... A61B 1/32
(52) U.S. Cl. ...................................... 600/210; 600/219
(58) Field of Search ............................. 600/210–214, 600/219, 201, 205, 222–224, 235

(56) References Cited

U.S. PATENT DOCUMENTS

| | | | | |
|---|---|---|---|---|
| 5,616,117 A | * | 4/1997 | Dinkler et al. | 600/232 |
| 5,688,223 A | * | 11/1997 | Rosendahl | 600/215 |
| 5,728,046 A | * | 3/1998 | Mayer et al. | 600/210 |
| 5,928,139 A | * | 7/1999 | Koros et al. | 600/205 |
| 6,096,046 A | * | 8/2000 | Weiss | 606/119 |
| 6,280,379 B1 | * | 8/2001 | Resnick | 600/220 |
| 6,302,842 B1 | | 10/2001 | Auerbach et al. | |
| 6,354,995 B1 | * | 3/2002 | Hoftman et al. | 600/219 |
| 6,416,467 B1 | * | 7/2002 | McMillin et al. | 600/224 |
| 6,431,246 B1 | * | 8/2002 | Peterson | 160/168.1 R |

* cited by examiner

*Primary Examiner*—Pedro Philogene
(74) *Attorney, Agent, or Firm*—Carter, DeLuca, Farrell & Schmidt, LLP.

(57) ABSTRACT

A multipurpose retractor is disclosed for use in surgical operations. The retractor can also be used as a speculum. The retractor is made from metal plates, springs, strings, hinges, rods and a worm gear system. The retractor can expand from having a very small diameter to a very large diameter. And at the same time it can produce substantial force or pressure to keep any orifice, birth canal, surgical incision open steadily and stably. The retractor can be easily collapsed after use within seconds using a worm gear system. The worm gear system provides considerable mechanical advantage and allows for the contraction of the retractor with little applied force by the hand. It also allows for control of the retractor to remain in a certain diameter size. A locking mechanism applied to the gear system prevents the retractor from unfolding and therefore the retractor remains stable. The spring system provides the retractor to open completely with great force and remain open.

20 Claims, 2 Drawing Sheets

MULTIPURPOSE CIRCULAR RETRACTOR

PRIORITY

This application claims priority to a U.S. Provisional Application filed on Nov. 20, 2001 and assigned U.S. Provisional Application Ser. No. 60/331,837, the contents of which are incorporated herein by reference.

BACKGROUND OF THE INVENTION

1. Field of the Invention

The present invention relates to a surgical retractor and its multipurpose use, particularly, a retractor that can be used as a speculum, and in a surgical procedure. This is a versatile retractor for maintaining any orifice of the body, small or large, open or patent.

2. Description of the Related Art

Many retractors are not capable of being used in many different kinds of procedures and surgical operations.

It is therefore one object of the present invention to provide a multipurpose retractor, i.e., a retractor that can be used in many surgical operations for retraction purposes, and as a speculum in obstetrics and other gynecological procedures.

SUMMARY OF THE INVENTION

The present invention provides a multipurpose retractor that can be used in any surgical operation. It can also be used as a speculum. The retractor is made from metal plates, springs, strings, hinges, rods and a worm gear system. The retractor can expand from having a very small diameter to a very large diameter if its geometrical configuration is a cylinder. The retractor is able to produce a suitable force and exert adequate pressure to keep any orifice, birth canal, surgical incision open steadily and stably. The retractor can be easily collapsed after use within seconds using a worm gear system as known in the art.

The worm gear system provides considerable mechanical advantage and allows for the contraction of the retractor with little applied force by the hand. It also allows for control of the retractor to remain in a certain diameter size. A locking mechanism applied to the gear system prevents the retractor from unfolding and therefore the retractor remains stable. The spring system provides the retractor to open completely with great force and remain open. The worm gear system and the strings control the rate of expansion of the retractor. The string system reels in all the metal plates allowing for the contraction of the retractor. The retractor is preferably made entirely from metal making it suitable for sterilization and therefore it can be categorized as a reusable retractor. It is, however, contemplated to manufacture the retractor of the present invention entirely from plastics and therefore it can be categorized as a disposable retractor.

The retractor has a multipurpose use, it can be used as a speculum, it can be used to help intubate someone, and it can be used to retract any surgical incision and any orifice that needs to remain open. The retractor has no sharp edges, and all areas of the retractor are smooth and polished. This prevents lacerations and other injuries to the patient and surgeon, and also allows for the smooth entry and exit of the retractor from any opening.

BRIEF DESCRIPTION OF THE FIGURES

The invention will be described in greater detail with reference to the accompanying drawings in which like elements bear like reference numerals, and wherein.

DETAILED DESCRIPTION OF THE INVENTION

The multipurpose circular retractor of the present invention is a surgical instrument that utilizes gears, springs, metal plates, metal rods and metal strings. These components provide the retractor with flexibility and high strength, and allow it to retract or expand any opening that needs to be patent during medical and surgical procedures.

Construction of the inventive retractor 5 is as follows: two metal plates 10A and 10B made from stainless steel, titanium, titanium alloy, aluminum, hard plastic, and/or any other metal, or material, are placed adjacent to each other, see FIG. 1. The plates 10A & 10B are specially designed to have hinges 20 on either side. The curled metal hinges 20 also have holes inside on the sides, see FIG. 1. Then the springs 30 are placed inside the curled metal hinges articulating with the holes inside the hinges, see FIG. 1.

Figure 1:
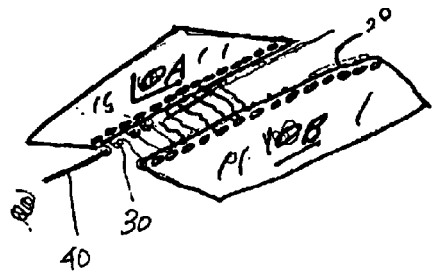
FIG. 1 is a perspective view showing the metal plates, hinges, springs, rods, and strings of the retractor in accordance with the present invention.

There are many such springs fitted along the length of the metal plate, see FIG. 1. A metal rod 40 inserted through the hinges and the spring 30 such that the two metal plates 10A & 10B articulate with each other in perfect alignment. Many plates are joined together contiguously conforming into a cylindrical structure, see FIG. 2. At all the articulating points the rod's ends are capped in a smooth and stable manner, see FIG. 1.

Figure 2:
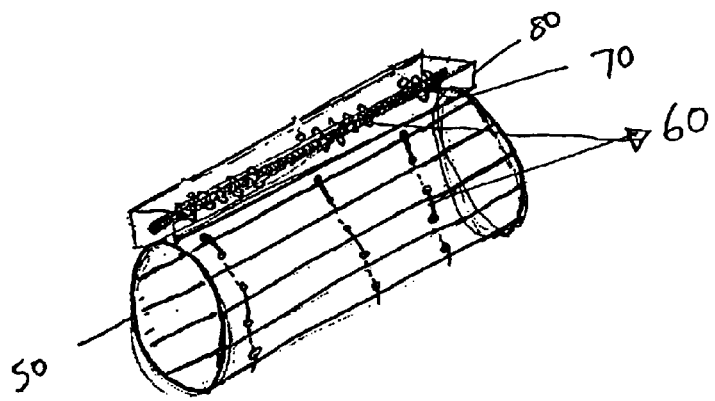
FIG. 2 is a perspective view showing the assembly of the metal plates, hinges, springs, rods, and strings into a cylindrical configuration in accordance with the present invention.

In this manner a cylinder metal piece 50 is created, see FIG. 2. Then holes 50A are drilled into each metal plate and each one of them align with holes of the adjacent plate, see FIG. 1. High tensile semi flat strings 60 are passed in between all these plates in a cylindrical pattern as shown by FIG. 2. One end of these strings 60 is anchored to the last plate of the cylindrical apparatus and the other end is anchored to main rod 70, see FIG. 2. This rod 70 is placed in the metal box 80 with two holes on its sides, see FIG. 2. The box 80 is anchored to cylindrical metal piece plate 50, see FIG. 2, at one end. Perpendicular to one end of metal box 80 there is a handle 90, see FIG. 3. Another metal plate 100 is joined on all sides to the handle 90, see FIG. 3.

Figure 3:
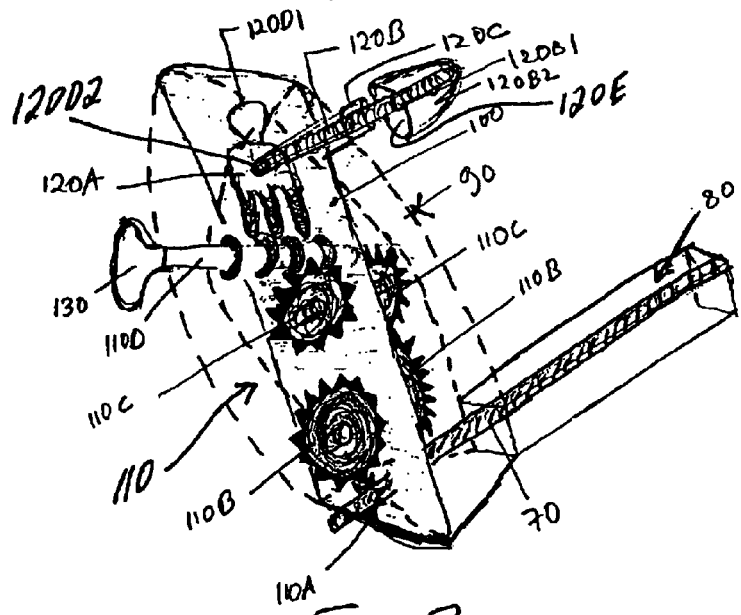
FIG. 3 is a perspective view showing the assembly of the handle, the gear system, and the lock system of the retractor in accordance with the present invention.

A worm gear system 110, and a lock mechanism 120 are made to fit inside the handle 90, see FIG. 3. The gear consists of a small gear 110A attached to the main rod 70, see FIG. 3. The small gear 110A is attached to a medium-sized gear 110B, which is attached to a larger gear 110C, see FIG. 3. The larger gear 110C is attached to worm gear 110D, see FIG. 3.

A smooth knob 130 is attached to the worm gear 110D, see FIG. 3. The knob 130 protrudes outside the hand held metal box 80, see FIG. 3. The lock mechanism 120 has a metal teeth plate-like piece in 120A, attached to a metal rod 120B that penetrates the inside metal plate 100 and the outside of the metal handle 90, see FIG. 3. The toothed 120A metal piece can be made to articulate with the worm gear 110D, see FIG. 3. Another metal clip like piece 120C, straddles the rod of the metal tooth 120B, see FIG. 3. At one end of the rod 120B there is screw thread created 120B1, see FIG. 3. Engulfing the 120B1 rod threads is a metal cap 120B2 which has an inner surface threaded for screwing on to rod 120B1, see FIG. 3.

The metal rod 120B can be made to switch between two holes 120D1 and 120D2. The outer distal distant hole 120D1 will keep 120A metal teeth away from the worm gear 110 and therefore in an unlocked position for the retractor 5. The locked position entails bringing 120B rod onto the second hole 120D2 proximally. This causes 120A metal teeth piece to jam onto the worm gear 110C. Now the metal clip 120C can be inserted into another hole 120E and the cap 120B2 can be screwed onto 120B1 to the lock the retractor 5. The final configuration of the embodiment looks like that shown by FIG. 4 in the contracted configuration (non-expanded configuration), and like that shown by FIG. 5 in the expanded configuration.

Figure 4:
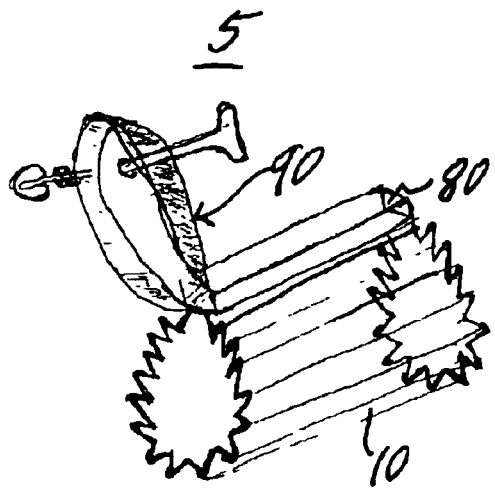
FIG. 4 is a perspective view showing the retractor of the present invention in a retracted or non-expanded configuration.
Figure 5:
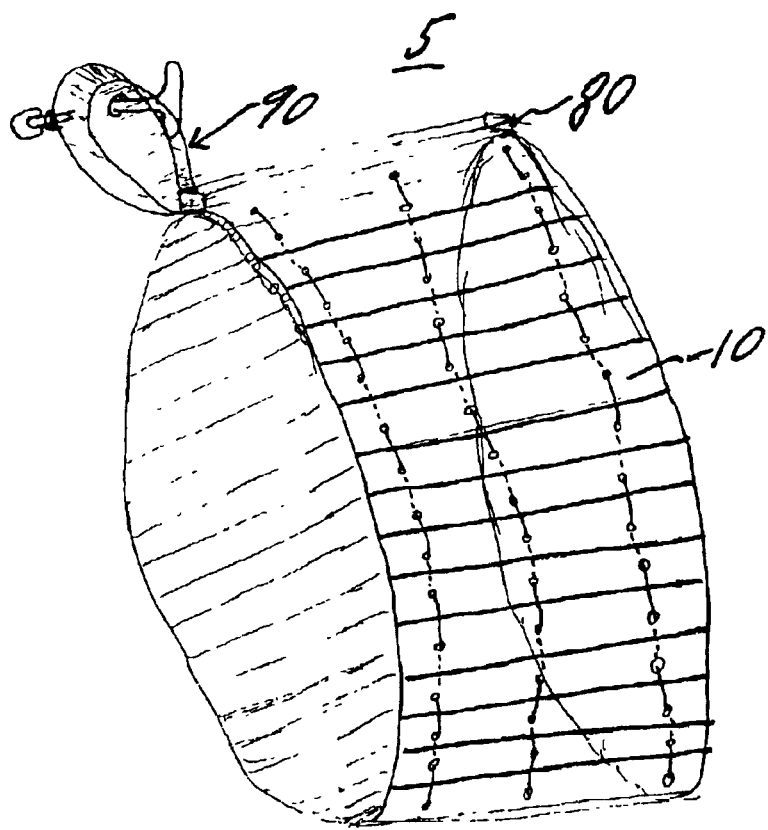
FIG. 5 is a perspective view showing the retractor of the present invention in an expanded configuration.

Before use, the retractor 5 is usually kept in contracted form as shown by FIG. 4. During use when it is inserted into a body orifice, for example the birth canal, or the oral cavity to intubate, or to retract a surgical incision, then the smooth knob 130 is turned in such a manner as to unwind the worm gear system 110. Thus the main rod 70 also turns releasing strings 60. As the controlling strings unleash the centrifugal force generated by the springs 30 will cause the retractor 5 to open.

In one embodiment, the retractor 5 enlarges or expands to more than ten times its diameter. The retractor 5 is locked at a desired diameter size using lock mechanism 120.

Once the operation of the retractor 5 is no longer needed, then, first, the lock mechanism 120 is used to unlock the retractor 5 and the smooth knob 130 is turned in an opposite direction than when the retractor 5 was expanded, thus winding the worm gear system 110 and the strings 60, to place the retractor 5 in the non-expanded configuration, see FIG. 4. The worm gear system offers 110 a mechanical advantage and allows for operation of the retractor 5 to be conducted with ease.

It is envisioned that the inventive retractor 5 can be designed with many different shapes, sizes and lengths to meet the needs of different kinds of retractions. Also, the retractor 5 is designed to have smooth metal edges as to not cause any lacerations or other injury to the patient. After the surgical procedure or other procedure, the retractor 5 can be autoclaved and sterilized. But if it is completely made from plastic, then the retractor 5 can be disposed. The retractor 5 can be also made from a combination of metal and plastic.

The inventive retractor 5 can also be used in abdominal surgeries, thoracic surgeries, obstetrics and gynecology surgery, ENT surgery, brain surgery, eye surgery, trauma surgery, orthopedic surgery, urology surgery, heart surgery, and other procedures that may not necessarily involve surgery. It can be used as a speculum or help in laparoscopic procedures. It can also be used in supporting fractured bones and can act as a cast in orthopedic cases. The inventive retractor 5 can also be miniaturized to be used as a stent. Besides surgical and medical uses, the retractor 5 can also be used in many other applications, such as engineering and scientific applications. Further, the retractor 5 can be designed to assume any geometrical configuration, such as a cylindrical, rectangular, triangular, ovular, elliptical, trapezoidal, pentagonal, hexagonal, octagonal, etc.

It will be further apparent to one skilled in this art that the improvements provided for in the present invention, while described with relation to certain specific physical embodiments also lend themselves to being applied in another physical arrangements not specifically provided for herein, which are nonetheless within the spirit and scope of the invention taught here.

What is claimed is:

1. A surgical device for expanding an orifice, the device comprising:
    a plurality of plates interconnected by at least one string of a connection mechanism and defining an opening having a first perimeter, the plurality of plates being dimensioned and configured to be at least partially insertable within a body part; and
    an operating mechanism in operative communication with the connection mechanism for controlling the orientation and position of each of the plurality of plates with respect to adjacent plates of the plurality of plates, the operating mechanism being operable to move the plurality of plates from a first position having a first perimeter, to a second position having a second perimeter, wherein the second perimeter is substantially larger than the first perimeter.

2. The device according to claim 1, wherein the at least one string passes through holes in proximity to at least one edge of each of the plurality of plates, the at least one string being received by the operating mechanism for controlling the orientation and position of each of the plurality of plates for controlling an amount of space surrounded by a geometrical shape formed by the plurality of plates.

3. The device according to claim 1, wherein the operating mechanism includes at least one handle for directly controlling at least one component of the operating mechanism for controlling the orientation and position of each of the plurality of plates.

4. The device according to claim 1, wherein the operating mechanism includes a worm gear mechanism.

5. The device according to claim 1, wherein the operating mechanism includes a locking mechanism for locking each of the plurality of plates within a particular orientation and position with respect to the other plurality of plates.

6. The device according to claim 5, wherein the locking mechanism locks each of the plurality of plates in the particular orientation and position.

7. The device according to claim 1, wherein the device is made from at least one of metal and plastic.

8. The device according to claim 1, wherein the device is selected from the group consisting of a retractor, a stent, and a speculum.

9. A surgical device for expanding an orifice, the device comprising:
    a plurality of plates configured for expanding from a flat orientation to a non-flat orientation, the plurality of plates being dimensioned and configured to be at least partially insertable within a body part; and,
    an operating mechanism having at least one string in operative communication with the plurality of plates for controlling the orientation of the plurality of plates; and,
    wherein the at least one string passes through holes in proximity to at least one edge of each of the plurality of plates, the at least one string being received by the operating mechanism for controlling the orientation of the plurality of plates.

10. The device according to claim 9, wherein the operating mechanism includes at least one handle for directly controlling at least one component of the operating mechanism for controlling the orientation of the plurality of plates.

11. The device according to claim 9, wherein the operating mechanism includes a worm gear mechanism.

12. The device according to claim 9, wherein the operating mechanism includes a locking mechanism for locking each of plurality of plates within a particular orientation and position with respect to the other plurality of plates.

13. The device according to claim 12, wherein the locking mechanism locks each of the plurality of plates in the particular orientation and position.

14. The device according to claim 9, wherein the device is made from at least one of metal and plastic.

15. The device according to claim 9, wherein the device is selected from the group consisting of a retractor, a stent, and a speculum.

16. A method for expanding an orifice, the method comprising the steps of:

providing a plurality of plates interconnected by a connection mechanism having at least one string, the plurality of plates being dimensioned and configured to be at least partially insertable through a body part;

inserting at least a portion of the plurality of plates into a body part; and selectively operating the connection mechanism for controlling the orientation and position of the plurality of plates with respect to adjacent plates of the plurality of plates to form a geometrical shape.

17. The method according to claim 16, wherein the at least one string passes through holes in proximity to at least one edge of each of the plurality of plates, the at least one string being received by an operating mechanism for controlling the orientation and position of each of the plurality of plates for forming the geometrical shape.

18. The method according to claim 16, wherein the step of selectively controlling the connection mechanism includes rotating at least one handle for controlling the connection mechanism for controlling the orientation and position of each of the plurality of plates.

19. The method according to claim 16, further comprising the steps of locking each of the plurality of plates within a particular orientation and position with respect to the other plurality of plates.

20. The method according to claim 16, wherein the geometrical shape is a cylinder and the step of selectively controlling includes the step of controlling the diameter of the cylinder.

* * * * *